United States Patent [19]
Jacobs

[11] Patent Number: 6,120,775
[45] Date of Patent: Sep. 19, 2000

[54] STREPTOCOCCUS EQUI VACCINE

[75] Inventor: Antonius Arnoldus Christiaan Jacobs, Kessel, Netherlands

[73] Assignee: Akzo Nobel N.V., Arnhem, Netherlands

[21] Appl. No.: 09/123,735

[22] Filed: Jul. 28, 1998

[30] Foreign Application Priority Data

Jul. 29, 1997 [EP] European Pat. Off. .............. 97202365
Sep. 24, 1997 [EP] European Pat. Off. .............. 97202925

[51] Int. Cl.$^7$ ..................... A61K 39/09; A61K 49/00; A61K 39/02; A01N 63/00; C12N 1/20
[52] U.S. Cl. ................... 424/244.1; 424/9.2; 424/184.1; 424/829; 424/237.1; 424/93.44; 435/173.1; 435/253.4; 435/885
[58] Field of Search ................... 424/9.2, 829, 184.1, 424/237.1, 93.44, 244.1; 435/173.1, 253.4, 885

[56] References Cited

U.S. PATENT DOCUMENTS

| | | |
|---|---|---|
| 4,110,433 | 8/1978 | Purdy . |
| 4,521,513 | 6/1985 | Russell . |
| 4,788,059 | 11/1988 | Usdin . |
| 5,183,659 | 2/1993 | Timoney . |
| 5,389,368 | 2/1995 | Curtiss, III .............................. 424/93.2 |
| 5,672,345 | 9/1997 | Curtiss, III .............................. 424/93.2 |
| 5,895,654 | 4/1999 | Hartford et al. . |

FOREIGN PATENT DOCUMENTS 0 786 518  7/1997  European Pat. Off. .
WO 87/00436  1/1987  WIPO .

OTHER PUBLICATIONS

Goodman et al., The Pharmacological Basis of Therapeutics, 8th edition, p. 8, 1990.
Tortora et al., Microbiology: An Introduction, 3rd edition, p. 158, 1989.
Challacombe, S.J. et al. "Salivary antibody responses in rhesus monkeys immunized with *Stretococcus mutans* by the oral submucosal or subcutaneous routes." Archives of Oral Biology, 1979, vol. 24, pp. 917–924.
Wallace et al, Vet. Immunol & Immunopathol 48:139–254, 1995.
Sheoran et al. Vet. Immunol & Immunopathol, 59:239–251, 1997.
Loving, Equine Practice, 21/9: 6,8,10, Oct. 1999.
Jorm, Aust. Vet. J. 67:436–439, 1990.
Cornell University, Equine Practice 9/3:23–25, Mar. 1987.

*Primary Examiner*—Nita Minnifield
*Attorney, Agent, or Firm*—Michael G. Sullivan

[57] ABSTRACT

The present invention relates to a method of systemically administering a vaccine comprising live attenuated bacteria of the species *Streptococcus equi* in order to protect against *Streptococcus equi* infection.

6 Claims, No Drawings

STREPTOCOCCUS EQUI VACCINE

FIELD OF THE INVENTION

The present invention relates to the use of live attenuated *Streptococcus equi* for the manufacture of vaccines.

BACKGROUND OF THE INVENTION

*Streptococcus equi* has been known for a long time to be the cause of an acute disease of the upper respiratory tract in horses (Sweeney et al., Compendium Equine 9: 689–693 (1987)) This highly contagious disease is characterised by fever, mucopurulent nasal discharge, lymphadenopathy and subsequent abscessation of the lymph nodes of the head and the neck (Sweeney et al., Compendium Equine 9: 845–851 (1987)). The swelling of the lymph nodes is often so severe that the airways become obstructed. This phenomenon explains the common name of the disease; strangles.

The disease is only fatal in a minority of the cases, as described by Sigmund (Sigmund, O. H. and Fraser, C. M. eds.: The Merck Veterinary Manual, 5$^{th}$ Ed. Merck and Company Inc., Rahway, N.J.: 313–315 (1979)). Contrary to this, morbidity is generally high, and can be as high as 100% in susceptible populations.

Vaccines against the disease have also been known for a long time (Bazely, P. L.; Austr. Vet. J. 16: 243 (1940)) and (Bazely, P. L.; Austr. Vet. J. 18: 141–155 (1942). Until recently, only two kinds of vaccines were available: a) vaccines based on classical bacterins and b) subunit vaccines based on the M protein, an immunogenic protein. Both kinds of vaccine have their own severe drawbacks. Bacterins are notorious for their adverse reactions and are known to provide relatively little protection (Subcommittee on the Efficacy of Strangles Bacterin, Report, American Association of Equine Practitioners). Srivastava and Barnum (Can. J. Comp. Med. 45: 20–25 (1981)) demonstrated that commercial and autologous killed whole cell vaccines are not capable of inducing a sufficient level of antibodies to protect against strangles.

Woolcock Austr. Vet. J. 51: 554–559 (1975) showed that a vaccination scheme of three doses at ten day intervals is essential to obtain at least partial protection. Boschwitz comes to the conclusion for the major immunogenic subunit of *S. equi*, the M protein, that antibodies against this antigen are not sufficient to protect horses from natural or experimental infections (Cornell Vet. 81: 25–36 (1991)).

In a comparative study, in which both whole cell and M subunit vaccines were compared, Srivastava and Barnum, Can. J. Comp. Med. 49: 351–356 (1981) again reported the very weak results with these kinds of vaccines: repeated booster vaccinations are necessary to obtain reasonable antibody titres and the longevity of the high titres is short. Further booster vaccinations should be given at least once a year (Sweeney et al., Compendium Equine 9: 845–851 (1987)). Moreover, there is hardly any correlation between antibody titers and protection. Even recent papers, in which killed *S. equi* was administered intraperitoneally or orally describe only partial protection against challenge with live *Streptococcus equi* (Wallace et al, Vet. Immunol. and Immunopath. 48: 139–154 (1995). Classical vaccines based on bacterins or subunits are e.g. available trough Forth Dodge Laboratories, Coopers Animal Health and the Mobay Company (U.S. Pat. No. 4,944,942).

Mounting evidence in the literature indicates that immunity to *S. equi* is local, rather than systemic. The paramount importance of local immunity in conferring protection against streptococcal infection is i.a. well-documented by Bessen and Fischeffi, in J. Exp. Medicine 167: 1945–1950 (1988), and in Infect. and Immun. 56: 2555–2672 (1988)). It has been established that local immunity is mediated by mucosal antibodies as was summarised i.a. by Bernadette (J. Gen. Microbiol. 137:2125–2133 (1991).

And since the nasopharynx is the natural port of entrance for *Streptococcus equi*, it is now generally accepted that successful vaccination necessarily requires stimulation of the nasopharyngial immune response. (Galan et al., Inf. Immun. 47: 623–628 (1985), (Galan et al., Inf. Immun. 54: 202–206 (1986), (Timoney et al., In Kimura, y., Kotami, S., Shiokawa, y. (ed.). Recent advances in streptococci and streptococcal diseases. Reed Books, Danbury, N.H.).

The well-established importance of direct stimulation of the nasopharyngial immune response has contributed greatly to the current opinion, that only the intranasal application of a vaccine can provide at least partial protection.

A general problem with intranasally given live attenuated vaccines is the fact that the vaccine does not stay in the nose, but leaks away through sneezing, leaking and the like. This is an unwanted situation for two reasons: most of the vaccine virus becomes spread into the environment, and an overdose must be give to assure a sufficient level of vaccination. These disadvantages are however accepted in practice since as motivated above intranasal vaccination is currently considered the only way to obtain at least partial protection.

A live attenuated strain has to our knowledge only been described in WO/87/00436. In this application it is once more stated that intranasal/oral vaccination with live *Streptococcus equi* is the only way to obtain possible protection, since other routes of vaccination and/or the use of subunit vaccines are known to be ineffective. The disadvantage of this vaccine, however, is, that it is a non-encapsulated mutant. Therefore, no immune response against the lipopolysaccharide moiety of the bacterium is obtained.

SUMMARY OF THE INVENTION

It is an objective of the present invention to circumvent the problems encountered with the above-mentioned live attenuated vaccines.

It was surprisingly found, that in defiance of the current opinion about the importance of direct stimulation of the nasopharyngial immune response, a virtually perfect protection against strangles can be obtained if a vaccine based upon a live attenuated *Streptococcus equi* strain is administered systemically, instead of locally. This very high level of protection is even more unexpected in view of the fact that the degree of protection obtained when the same attenuated live strain is given intranasally is dramatically less complete.

DETAILED DESCRIPTION OF THE INVENTION

Thus, the present invention provides the use of a live attenuated bacterium of the species *Streptococcus equi* for the manufacture of a vaccine for systemic application for combating *Streptococcus equi* infection.

Systemic application is considered to be the opposite of local application. Local application, the application currently considered to be the only effective way of vaccination against *Streptococcus equi*, means application of the vaccines on the mucous membranes. Mucosal membranes are in direct contact with the outside world and they are found e.g. in the digestive tract, the nasopharynx and the vagina.

Several local applications are currently in use: intranasal, oral and intravaginal application.

Systemic application, the application route to which the invention relates, is an application in which the vaccine is brought into or below the dermis of the animal to be vaccinated. Well-known examples of systemic application are the intramuscular vaccination and the subcutaneous application. Other routes of systemic vaccination are e.g. intradermal vaccination, intravenous vaccination and intraperitoneal vaccination. Intradermal vaccination has become an attractive way of vaccinating nowadays, because the vaccine can easily be administered by spraying through a high-pressure nozzle which is placed on the skin. Another attractive way of administration of the vaccine is intramuscular vaccination. In the first place because many practitioners are used to this way of vaccination. Moreover, intramuscular vaccination has the advantage that the vaccine is slowly released from the muscles into the blood. Thus the immune system is triggered by the vaccine for an extended period of time.

Therefore, in a preferred form the invention relates to the use of a live attenuated bacterium of the species *Streptococcus equi* for the manufacture of a vaccine for intramuscular application.

Live attenuated vaccines often have a relatively high level of virulence left. The higher the virulence level, the higher the level of immunity induced. On the other hand, evidently the disadvantage of high virulence levels is, that the pathogenic effect of virulent vaccine strains is closer to that of field infection. Vaccination with live *Streptococcus equi* vaccines in practice means balancing between good protection but adverse reactions at the site of immunisation, or no immunisation reactions but low efficacy of the vaccine.

Therefore, a way of vaccinating with live attenuated *Streptococcus equi* that on the one hand gives sufficient protection, and on the other hand avoids the adverse reactions at the site of vaccination is highly desirable.

It was surprisingly found, that vaccination in soft tissue, below the mucosa, unexpectedly solves this problem. When the live attenuated vaccine is administered in such tissue, all the advantages of the systemic administration route are maintained and additionally no or only minor local reactions at the site of administration are found. Suitable tissues for such vaccinations are e.g. the mouth. Such tissues all have a mucosal layer. Vaccination in these tissues can be done systemically, and therefore below this layer. Vaccination of the tissue below the mucosa is generally called submucosal vaccination.

Therefore, in another preferred form the invention relates to the use of a live attenuated bacterium of the species *Streptococcus equi* for the manufacture of a vaccine for submucosal application.

When vaccination takes place in the mouth, the vaccine is advantageously administered submucosally into the cheek, or the upper or lower lip. Around the mouth, the lips of a horse are the easiest place to vaccinate from the point of animal handling. Therefore, in a more preferred form the invention relates to the use of a live attenuated bacterium of the species *Streptococcus equi* for the manufacture of a vaccine for labial application.

As a live attenuated Streptococcus strain, every strain can be used that possesses an attenuated character to the level that it does not cause unacceptable side-effects. The attenuated character may be obtained trough classical attenuation methods such as growth under different temperatures, growth in the presence of mutagenic agents, high energy radiation, UV-light and the like. The attenuated character may also be obtained by recombinant DNA techniques, e.g. the deletion of virulence factors.

During the manufacturing of the vaccine a pharmaceutically acceptable carrier can also be added. One possible carrier is a physiological salt solution. Another pharmaceutically acceptable carrier is for instance the growth medium used for growing the bacterium.

If desired, an adjuvant and possibly one or more emulsifiers such as TWEEN and SPAN are also incorporated in the live vaccine. Suitable adjuvants are, for example, vitamin E acetate solubilisate, aluminium hydroxide, -phosphate or -oxide, (mineral) oil emulsions such as BAYOL and MARCOL 52, and saponins. Thus in an even more preferred form of this embodiment, in addition to the live attenuated bacterium, an adjuvant is used for the manufacture of said vaccine.

In a still even more preferred form of this embodiment, in addition to the live attenuated bacterium another pathogen or antigenic material from another pathogen is used for the manufacture of said vaccine. Such a pathogen may e.g. be another bacterium or a parasite. Also it can be of viral origin. Usually, the other pathogen or antigenic material thereof will be a horse pathogen. A vaccine that comprises such an additional attenuated pathogen or antigenic material from another attenuated pathogen has the advantage that it induces protection against several infections at the same time. In an even better form, the pathogens or antigenic material thereof is selected from of Potomac fever agent, *Rhodococcus equi, Clostridium tetanii, Mycobacterium pseudomallei, Streptococcus zoöepidemicus*, Vesicular Stomatitis virus, Borna disease virus, Equine influenza virus, African horse sickness virus, Equine arteritis virus, Equine herpesvirus 1–4, Infectious anaemia virus, Equine encephalomyelitis virus and Japanese B encephalitis virus.

In a most preferred form, the bacterium used for the manufacture of the vaccine according to the present invention is the *Streptococcus equi* strain TW 928 as disclosed in European Patent Application 0786518. This strain was deposited on Dec. 12, 1995 in connection with this application under number CBS 813.95 with the Centraalbureau voor Schimmelcultures, P.O.box 273, 3740 AG Baam, The Netherlands.

There are several ways to store live attenuated *Streptococcus equi*. Storage in a refrigerator is e.g. a well-known method. Also often used is storage at −70° C. in a buffer containing glycerol. Bacteria can also be kept in liquid nitrogen. Freeze-drying is another way of conservation. Freeze-dried bacteria can be stored and kept viable for many years. Storage temperatures for freezedried bacteria may well be above zero degrees, without being detrimental to the viability. Freeze-drying can be done according to all well-known standard freeze-drying procedures. Optional beneficial additives, such as e.g. skimmed milk, trehalose, gelatin or bovine serum albumin can be added in the freeze-drying process. Therefore, in a most preferred form, the vaccine, once manufactured, is in a freeze-dried form.

The doses that can be given depend partially on the level of attenuation. Generally doses ranging between $10^3$ and $10^{10}$ are suitable doses. The vaccine can be administered in principle in all suitable muscles, but most conveniently it is administered in the muscles of the neck, and the hind and fore legs.

EXAMPLES

Example 1

Preparation of Live Attenuated Vaccine

Live attenuated *Streptococcus equi* strain TW 928 was grown under standard conditions in medium containing:

tryptose 5.0 g

Neutral soy peptone 5.0 g

Yeast extract 2.5 g

Beef extract 5.0 g

D-glucose 10.0 g

Ascorbic acid 0.5 g

B-glycerolphosphate 19.0 g

Magnesiumsulphate 7H2O 0.25 g

Aqua dest. 1 liter

When used as a live attenuated strain, the bacteria were administered in the above mentioned medium. When given as an inactivated vaccine, the cells were first inactivated in 0.02% benzalkonium chloride.

Experimental Design

Twelve horses (13–16 months of age) with no history of strangles were divided into 4 groups of three horses each. At day 0, 21 and 42, horses of group I were vaccinated intranasally with 2×1 ml live *S. equi* vaccine containing $10^{9.5}$ CFU/ml (1 ml into each nostril). Horses of group II were vaccinated intramuscularly in the neck with 2 ml of the same live *S. equi* vaccine, and horses of group III were vaccinated intramuscularly in the neck with 2 ml of an inactivated whole cell vaccine containing $5\times10^9$ CFU/ml in saponin adjuvant. The 3 horses of group IV were left untreated as unvaccinated challenge controls. At day 56 all 12 horses were challenged intranasally with 3 ml of a $10^{93}$ CFU/ml culture of *S. equi* strain Amica. Rectal temperatures were determined at least twice weekly before challenge and daily after challenge. During the whole experiment the horses were daily observed for any abnormalities by a biotechnician. After each vaccination the horses were daily observed for local or systemic reactions until any reactions had disappeared for two subsequent days. Clinically examination by a veterinarian was done regularly before challenge and daily after challenge. At 1 to 4 weeks after challenge (depending on clinical signs and or condition) the horses were killed and subjected to complete post-mortem investigation with special attention to signs of strangles and samples were taken for reisolation of *S. equi*.

Clinical Signs

One month before first vaccination the horses were housed together to exchange microbiological flora. At day of first vaccination the horses had either no clinical signs or slight upper respiratory signs (e.g. nasal discharge) but further were in a good condition. After the vaccinations (until challenge) the horses had either no clinical signs or the same upper respiratory tract signs as before vaccination.

After challenge all 3 control horses, all 3 intranasally live vaccinated horses as well as all 3 horses that were vaccinated intramuscularly with the inactivated vaccine, developed clear signs of strangles characterised by sudden high temperatures, swollen lymph nodes of the head and the neck and purulent nasal discharge (where the last group appeared slightly less affected compared to the controls). In sharp contrast, the intramuscularly live vaccinated horses remained completely free from signs of strangles. The only signs observed were occasionally mild upper respiratory tract signs (i.e. same signs as observed before challenge and/or vaccination). The clinical scoring system is described in table 1. The clinical scores are summarised in Table 2. The total clinical score after challenge is obtained by addition of the clinical scores of each observation day after challenge, for each of the survived days.

Result: as is clear from table 2, intramuscular vaccination with a live attenuated *Streptococcus equi* vaccine reduces the clinical effects of a virulent *Streptococcus equi* challenge infection with 98%, whereas intranasal vaccination with the same vaccine only reduces the clinical effects with only 26%. Vaccination with inactivated cells of the same vaccine strain reduces the effects of challenge with 39%. Intramuscular vaccination with a live attenuated *Streptococcus equi* vaccine gives contrary to intranasal vaccination or vaccination with inactivated vaccine, a virtually complete protection against infection with virulent *Streptococcus equi* strains.

β-haemolytic streptococci in Nasal Washes

The first week after challenge *S. equi* was isolated in low numbers from only a few horses. Thereafter, the frequency and numbers strongly increased except for the intramuscularly live vaccinated horses and seemed to correlate with the presence of purulent nasal discharge, possibly originating from ruptured lymph node abscesses. The identity of these isolates was confirmed to be the challenge strain by using PCR.

Result: intramuscular application of live attenuated *Streptococcus equi* vaccines prevents spilling of vaccine into the environment and provides better dosage possibilities.

Post-Mortem Examination, Bacteriology and Histology

The post-mortem findings confirmed the clinical findings: i.e. all 3 intramuscular live vaccinated horses appeared completely free from macroscopic or microscopic signs of strangles and except for the vaccine injection site, *S. equi* was not reisolated, whereas all other horses (except for horse 35) showed one or more (strongly) enlarged and abscessed lymph nodes from which *S. equi* was isolated. Microscopic examination of the retropharyngeal lymph nodes of horse 35 showed that this horse also had a (mild) lymphadenitis from which *S. equi* also was isolated Result: the post-mortem results are fully in line with the clinical findings after challenge.

Example 2

Submucosal labial vaccination of horses with a live attenuated *S. equi* vaccine In this experiment the safety and efficacy of a live *S. equi* strain vaccine administered submucosally in the lip, was tested.

Preparation of a Vaccine *S. equi* Strain for Submucosal Labial Administration

The content of vials of freeze dried vaccine were dissolved in 1.0 ml aqua dest. One dose=200 μl of reconstituted vaccine. For priming vaccination the titre of the reconstituted vaccine was $3.0\times10^9$ CFU/ml and for booster vaccination $1.2\times10^9$ CFU/ml.

Test System

Animals

Ten Shetland type horses, seronegative for *S. equi,* 9–11 months old of age, with no history of strangles, were used for the experiment.

Experimental Set-Up

Vaccination/Challenge

After a two-week acclimatisation period, 5 horses were vaccinated submucosally in the lip (2 spots upper lip and 2 spots lower lip; 200 μl per spot) with the live attenuated vaccine strain. Five other horses were not vaccinated with the vaccine strain. At 4 weeks after priming vaccination the 5 vaccinates were boosted as described above. At 2 weeks after booster vaccination, all horses were challenged intranasally with *S. equi* strain Amica. After vaccination the horses were daily observed for any systemic or local reactions. At the end of the experiment or earlier in case of severe clinical signs, the horses were killed and subjected to post-mortem investigation.

Two weeks after the booster vaccinations, all horses were challenged intranasally: 2 ml of a fresh 6 hours culture of wild-type *S. equi* strain Arnica in M17 medium+glucose into each nostril. Viable count was determined immediately after challenge by plate counting. The viable count was $7.7 \times 10^8$ CFU/ml.

Local and Systemic Reactions

At day of vaccination Oust before), 6 hours after and then regularly during the experiment, the horses were observed for systemic and local reactions.

Rectal Temperatures

At day −1, 0 just before and 6 hours after vaccination), 1 and 2 after each vaccination and regularly after challenge (until post-mortem), rectal temperatures were measured by a biotechnician.

Results

Vaccination Reactions

At 6 hours after vaccination with the live attenuated vaccine strain an increase in rectal temperature was found. Mean temperatures increased ±1° C. compared to the controls at 6 hours after vaccination and ±1.7° C. compared to pre-vaccination temperatures. Temperatures were normal again the next day. After vaccination the horses appeared in a good condition and had a normal appetite and besides the effect on rectal temperature at 6 hours after vaccination no further systemic reactions were observed. After both vaccinations with the vaccine strain small transient local reactions were found. Most reactions had disappeared at 3 weeks after priming vaccination and at 2 weeks after booster vaccination.

Post-Mortem Examination and Bacteriology

When post-mortem examinations were done, it turned out that the vaccinated horses had no strangles and thus were protected. All other horses had strangles, i.e. abscesses in the retropharyngeal lymph nodes from which *S. equi* was reisolated or fibrotic retropharyngeal lymph nodes indicative for a more chronic stage of strangles, where the abscesses already were (partly) resolved. No residues or local tissues reactions were found at the sites of vaccination.

Discussion

From the results it is evident that an live attenuated *Streptococcus equi* vaccine induced complete protection against strangles (5/5 horses completely protected) whereas all other horses had strangles. After vaccination with the attenuated strain, the horses appeared to be in a good condition and had a normal appetite and besides a rise in rectal temperature at 6 hours after vaccination no further sysoemic reactions were observed. Furthermore, after the vaccinations only small transient local reactions were found which resolved completely (no residues or local tissue damage/reactions were found at post-mortem).

Conclusion

Submucosal vaccination in the lip with an attenuated live vaccine strain induced complete protection against strangles and is acceptable with regard to safety.

TABLE 1

Clinical scoring system.

| | | | |
|---|---|---|---|
| General impression | 0 = normal | Respiration type | 0 = costo-abdominal |
| | 1 = less active | | 2 = slightly abdominal |
| | 2 = slightly depressed | | 4 = abdominal |
| | 4 = depressed | | 6 = strongly abdominal |
| | 6 = severely depressed | Stridor | 0 = absent |
| Anorexia | 0 = normal | | 2 = slight |
| | 4 = loss of appetite | | 4 = moderate |
| Temperature | 0 = ≦38.5 | | 6 = severe |
| | 1 = 38.6 – 39.0 | Auscultation | 0 = normal |
| | 2 = 39.1 – 39.5 | | 2 = slight raies |
| | 3 = 39.6 – 40.0 | | 4 = dry or wet raies |
| | 4 = 40.1 – 40.5 | | 6 = area with no sound |
| | 5 = 40.6 – 41.0 | Lymph palpation | 0 = normal |
| | 6 = >41.0 | | 2 = slightly enlarged |
| Nasal discharge | 0 = absent | | 4 = moderately enlarged |
| | 1 = serous | | 6 = strongly enlarged or ruptured |
| | 2 = mucopurulent | | (if also painful, 1 point extra) |
| | 3 = purulent | Palpation larynx | 0 = no coughing |
| | (if excessive 1 point extra) | | 1 = one or two coughs |
| Ocular discharge | 0 = absent | | 2 = several coughs |
| | 1 = serous | | (if painful, 1 point extra) |
| | 2 = mucopurulent | Palpation trachea | 0 = no coughing |
| | 3 = purulent | | 1 = one or two coughs |
| | (if excessive 1 point extra) | | 2 = several coughs |
| Throat swelling | 0 = absent | | (if painful, 1 point extra) |
| | 2 = slight | Spontaneous cough | 0 = absent |
| | 4 = moderate | | 2 = after inspection |
| | 6 = severe | | 4 = before inspection |
| Respiration rate (min.) | 0 = ≦35 | Lamness | 0 = absent |
| | 1 = 36 – 45 | | 3 = detectable at walk |
| | 2 = 46 – 55 | | 6 = drags or jumps to carry lame legg |
| | 3 = 56 – 65 | | (for each swollen joint, independent of lameness 3 points extra) |
| | 4 = >65 | | |

TABLE 2

| Overview clinical scores after challenge | | | | | | | | |
|---|---|---|---|---|---|---|---|---|
| Vaccination | Horse | total clinical score after challenge | | | euthanized/killed | clinical score per observation day | | |
| group | number | total score | mean | % reduction | at post-chall. day | score/day | mean | % reduction |
| live | 35 | 140 | 218 | 26% | 21 | 6.7 | 17.3 | 16% |
| intranasally | 38 | 294 | | | 10 | 29.4 | | |
| | 39 | 220 | | | 14 | 15.7 | | |
| live | 34 | 9 | 6 | 98% | 21 | 0.4 | 0.3 | 99% |
| intramuscularly | 40 | 8 | | | 21 | 0.4 | | |
| | 41 | 2 | | | 21 | 0.1 | | |
| inactivated | 37 | 168 | 182 | 39% | 21 | 8.0 | 10.6 | 49% |
| intramuscularly | 42 | 249 | | | 14 | 17.8 | | |
| | 45 | 129 | | | 21 | 6.1 | | |
| control | 36 | 156 | 296 | 0% | 16 | 9.8 | 20.7 | 0% |
| | 43 | 295 | | | 14 | 21.1 | | |
| | 44 | 436 | | | 14 | 31.1 | | |

What is claimed is:

1. A method for protecting a horse against *Streptococcus equi* infection, comprising administering a vaccine comprising a live attenuated bacterium of the species *Streptococcus equi* and pharmaceutically acceptable carrier, wherein said vaccine is administered submucosally or labially.

2. The method according to claim 1, wherein in addition to the live attenuated bacterium the vaccine comprises an adjuvant.

3. The method according to claim 1, wherein in addition to the live attenuated bacterium the vaccine comprises another attenuated pathogen or antigenic material from another pathogen.

4. The method according to claim 3, wherein the other attenuated pathogen or antigenic material is selected or obtained from Potomac fever agent, *Rhodococcus equi, Clostridium tetanii, Mycobacterium pseudomallei, Streptococcus zooepidemicus*, Vesicular Stomatitis virus, Borna disease virus, Equine influenza virus, African horse sickness virus, Equine arteritis virus, Equine herpeavirus 1–4, infectious anaemia virus, Equine encephalomyelitis virus and Japanese B encephalitis virus.

5. The method according to claim 1, wherein the bacterium of said vaccine is the *Streptococcus equi* strain TW 928, deposited with the Centraalbureau voor Schimmelcultures at Baarn, The Netherlands under number CBS 813.95.

6. The method according to claim 1, wherein the vaccine is freeze-dried.

* * * * *